United States Patent [19]

Leistner et al.

[11] Patent Number: 5,166,355
[45] Date of Patent: Nov. 24, 1992

[54] PROCESS FOR PREPARING SUBSTITUTED 2,2'-METHYLENE-BIS-[6-(2H-BENZO-TRIAZOL-2-YL)-4-HYDROCARBYL-PHENOLS]

[75] Inventors: William E. Leistner, Atlantic Beach, N.Y.; Semyon Moshchitsky, Old Bridge; Mahmut Levent, Cliffside Park, both of N.J.

[73] Assignee: Fairmount Chemical Co., Inc., Newark, N.J.

[21] Appl. No.: 649,972

[22] Filed: Feb. 4, 1991

[51] Int. Cl.$^5$ .............................. C07D 249/20
[52] U.S. Cl. .................................... 548/260
[58] Field of Search .......................... 548/260

[56] References Cited

U.S. PATENT DOCUMENTS 4,937,348  6/1990  Kubota ..................... 548/259

Primary Examiner—Patricia L. Morris
Attorney, Agent, or Firm—Jones, Day, Reavis & Pogue

[57] ABSTRACT

A method is described for preparing compounds of Formula I and Formula II:

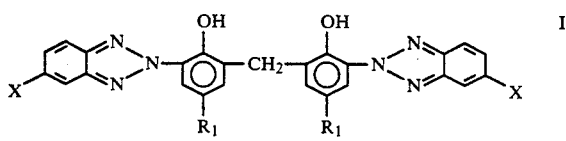

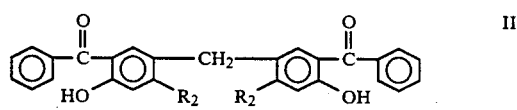

$R_1$ is an alkyl group of one to twelve carbon atoms or a cycloalkyl group of five to eight carbons, X is chloro or hydrogen, and $R_2$ is an alkoxy group having one to twelve carbons. In accordance with the method:

(a) a bis(dialkylamino)methane is formed, preferably by reacting a dialkylamine of the formula $HNR_3R_4$ (wherein $R_3$ and $R_4$ are independently alkyl groups having three or more carbons) and a solid formaldehyde material to produce the corresponding bis(dialkylamino)methane, (b) a monomer of Formula III or IV

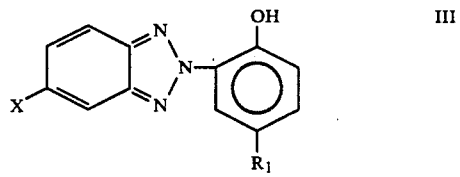

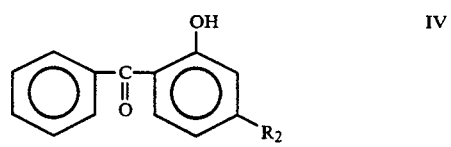

in which $R_1$ is an alkyl group of one to twelve carbons or a cycloalkyl group of five to eight carbons, X is chloro or hydrogen and $R_2$ is an alkoxy group having one to twelve carbon atoms, is mixed with an alkaline catalyst with heating at a temperature high enough to drive off the liquid formed in the reaction, (c) the product of steps (a) and (b) are combined and stirred at a temperature sufficient to drive the reaction for six to fourteen hours, and (d) thereafter the resulting compound of Formula I is collected.

18 Claims, No Drawings

PROCESS FOR PREPARING SUBSTITUTED 2,2'-METHYLENE-BIS-[6-(2H-BENZOTRIAZOL-2-YL)-4-HYDROCARBYL-PHENOLS]

BACKGROUND OF THE INVENTION a) Field of the Invention

This invention relates to an efficient method for preparing methylene bis (6-benzotriazolylphenols) and bis hydroxy benzophenones, in particular 2,2'-methylene-bis-[6-(2H-benzotriazol-2-yl)-4-hydrocarbyl phenols] and 5,5'-methylene bis-(2-hydroxy-4-alkoxy benzophenones). The method allows relatively rapid recovery of very pure product.

b) State of the Art 2,2'-Methylene-bis-[6-(2H-benzotriazol-2-yl)-4-(1,1,3,3-tetramethylbutyl)-phenol] is a known material having utility as an ultraviolet light absorber. It has been the subject of a number of patents including U.S. Pat. No. 4,937,348 (the "'348 Patent"). According to the '348 Patent, alkylidene bisphenols, such as 2,2'-methylene-bis-[6-(2H-benzotriazol-2-yl)-4-(1,1,3,3-tetramethylbuty)-phenol, may be prepared by (i) reacting a 4-hydrocarbyl-6-benzotriazolyl phenol with a primary or secondary amine and formaldehyde in an inert organic solvent to produce a Mannich base and (ii) reacting the base with itself or a 4-hydrocarbyl-6-benzotriazolyl phenol, preferably in the presence of an alkaline catalyst, such as a lower alkali metal alcoholate, an alkali metal hydroxide or an alkali metal alkaline salt. The reactions are carried out between 20° C. and 200° C., preferably between 30° C. and 150° C. The patent teaches removal of the solvent between steps (i) and (ii) to isolate the crude intermediate.

Preparation of 2,2'-methylene-bis-[6-(2H-benzotriazol-2-yl)-4-(1,1,3,3-tetramethyl)butyl)-phenol] is described in Example 3 of the '348 Patent. According to the process 4-(1,1,3,3-tetramethyl)butyl-6-benzotriazolyl-phenol was reacted with a secondary alkyl amine and paraformaldehyde in butanol and heated at reflux temperature for 24 hours. The solvent was distilled off. The resulting Mannich base and 4-(1,1,3,3-tetramethyl)-butyl-6-benzotriazolyl-phenol were dissolved in xylene and sodium methylate was added. The solution was heated under reflux at 140° to 150° C. for ten hours with a stream of nitrogen. The solvent was distilled off. The residue was recrystallized from xylene and then from n-heptane to produce a product melting at 200° C.

A similar method for making 5,5-methylenebis(2-hydroxy-4-alkoxybenzophenones) is disclosed in U.S. Pat. No. 4,186,151. According to that method, 2-hydroxy-4-alkoxybenzophenone is reacted with an amine and formaldehyde to form 2-hydroxy-4-alkoxy-5-aminomethylbenzophenone which is then dimerized or reacted with 2-hydroxy-4-alkoxybenzophenone in the presence of an alkaline catalyst.

In contrast to the prior art processes, the present invention is more rapid and efficient. Surprisingly, it has been found that by first condensing the formaldehyde and the dialkyl amine and then reacting the resulting bis(dialkylamino) methane with the monomer, the time required for the reaction is significantly reduced.

SUMMARY OF THE INVENTION

This invention provides a process for preparing methylene bis (substituted phenols) of Formula I or Formula II, such as 2,2'-methylene-bis-[6-(2H-benzotriazol-2-yl)-4-(1,1,3,3-tetramethylbutyl)-phenol] and 5,5'-methylene-bis-(2-hydroxy-4-methoxybenzophenone) respectively.

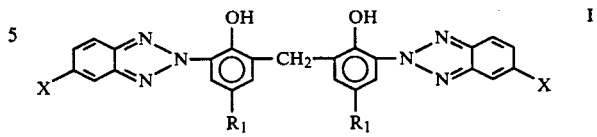

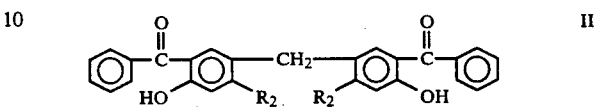

In Formula I each $R_1$ group is an alkyl group of one to twelve carbons or a cycloalkyl group of five to eight carbons and X is chloro or hydrogen. In Formula II $R_2$ is an alkoxy group of one to twelve carbon atoms. According to the process of the invention:

(i) a bis(dialkylamino)methane is synthesized, preferably by reacting formaldehyde and a dialkylamine;

(ii) in a separate reaction 4-hydrocarbyl-6-benzotriazolyl phenol or 2-hydroxy-4-alkoxybenzophenone as monomer and an alkaline catalyst are mixed and the mixture is heated to a temperature high enough to remove all liquid formed in the reaction;

(iii) thereafter the bis(dialkylamino)methane is added to the mixture with heating for several hours;

(iv) the reaction mixture is then neutralized and solvent for the salt product of the neutralization reaction is added in an amount sufficient to permit stirring.

The solid product produced is 2,2'-methylene-bis-[6-(2H-benzotriazol-2-yl)-4-hydrocarbyl phenol] or 5,5'-methylene bis(2-hydroxy-4-alkoxy benzophenone).

DETAILED DESCRIPTION OF THE INVENTION

In the practice of the present invention 2,2'-methylene-bis-[6-(2H-benzotriazol-2-yl)-4-hydrocarbyl phenols] can be prepared rapidly in pure form. In addition, [5,5'-methylene bis(2-hydroxy-4-alkoxy benzophenones] can be prepared.

The process of the present invention involves three reactions: (i) manufacture of a bis(dialkylamino)methane, preferably by condensation of formaldehyde and a dialkylamine, (ii) mixture of a 4-hydrocarbyl-6-benzotriazolyl phenol or a 2-hydroxy-4-alkoxy benzophenone with heating in the presence of a solvent, and (iii) reaction of the products of (i) and (ii) with heating. Upon completion of the reactions 2,2'-methylene-bis-[6-(2H-benzotriazol-2-yl)-4-hydrocarbyl phenol] or 5,5'-methylene bis(2-hydroxy-4-alkoxy benzophenone) is recovered by simply neutralizing the alkaline reaction mixture and dissolving the product of the neutralization reaction.

The method used to manufacture the bis(dialkylamino) methane is not critical. The bis(dialkylamino)methane used has the formula $CH_2(NR_3R_4)_2$ in which $R_3$ and $R_4$ are independently selected from alkyl groups of three or more carbons, commonly three to eight carbons. As noted, it is preferred that it be formed by condensing formaldehyde and a dialkylamine. More specifically, the formaldehyde used in the preferred reaction is a solid form of formaldehyde. Paraformaldehyde is particularly preferred, but other solid forms may be used.

The amine employed is a secondary amine having the formula $HNR_3R_4$ in which $R_3$ and $R_4$ have the previously indicated meanings. In general, the amines are those which are not miscible or soluble in water. The preferred amines or amino substituents on the bis(dialkylamino)methane are those in which $R_3$ and $R_4$ are the same with the most preferred being those in which $R_3$ and $R_4$ are both propyl, optimally n-propyl.

The monomer used in reaction (ii) is 4-(1,1,3,3-tetramethylbutyl)-6-benzotriazolyl phenol if 2,2'-methylene-bis-[6-(2H-benzotriazol-2-yl)-4-(1,1,3,3-tetramethylbutyl)-phenol] is the desired product. Alternatively, the appropriate 4-(hydrocarbyl-6-benzotriazolyl phenol of Formula III below is used to produce the corresponding 2,2'-methylene-bis-(6-benzotriazol-2-yl-4-hydrocarbyl phenol).

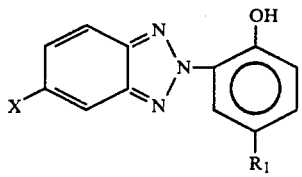

III

In Formula III, X is chloro or hydrogen and $R_1$ has the previously indicated meaning. Where the benzophenones are produced the monomers used have Formula IV.

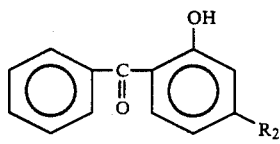

IV

In Formula IV, $R_2$ has the previously indicated meaning.

In preferred practice, in reaction (i), two moles of the amine rapidly condense with each carbon of the paraformaldehyde. The heat drives off the water formed in its azeotropic mixture with the excess amine. Generally temperatures above about 95° C. to 100° C. are sufficient to cause the water formed to be driven off. Temperatures of 95° to 130° C. are acceptable during this stage of the reaction, although temperatures of 120° C. to 130° C. are preferred.

The heating and stirring of the reactants should continue for a period of time sufficient to permit completion of the condensation of the formaldehyde and the amine and to drive off all water formed in that reaction. Commonly, as little as one or two hours is sufficient The temperature is then lowered to about 50° C. The excess amine is then removed by applying vacuum and raising the temperature to about 120° C.

The amount of amine used is generally slightly in excess of that required for complete reaction with the formaldehyde. Typically, about two to three moles of amine are used for each mole of carbon in the formaldehyde material used, preferably about 2.5 moles of amine for each mole of carbon. For example, with paraformaldehyde containing three carbons, the molar ratio of paraformaldehyde to amine would be approximately 1:7.5.

Once the condensation reaction is complete and the resulting water has been driven off, there is no need to recover the intermediate product from a solvent since no solvent was employed. Rather, the product of reaction (i) may be used directly in reaction (iii) below.

In reaction (ii) the appropriate monomer and an alkaline catalyst are combined typically in a solvent for the monomer. Generally the monomer is first fully dissolved in the solvent, commonly by stirring the two together at 30° to 80° C., preferably 60° C. The catalyst is then mixed in until it too is fully dissolved. The water or other liquid present as a result of reaction (ii) is then distilled off by heating. When sodium hydroxide is the catalyst, water is present and heating is effected at temperatures greater than about 100° C., preferably 130° C. to 150° C. In the case of alcoholate catalyst, the heating must be sufficient to distill off the alcohol present in the reaction.

The catalyst may be any alkaline catalyst of the type known to be suitable for promoting formation of the bis phenol. The preferred catalyst is sodium hydroxide. Examples of other suitable catalysts are lower alkali metal alcoholates, such as sodium methylate and ethylate; alkali metal hydroxides, such as sodium, potassium and lithium hydroxide; alkali metal amides, such as sodium amide and alkaline salts, such as potassium and sodium carbonate. The amount of the alkaline catalyst is not critical, and small amounts are usually sufficient. A preferred amount is within the range from 0.01 to 5 moles, preferably from 0.1 to 1 mole, per mole of monomer. In the most preferred practice, about 0.1 mole of catalyst is used for each mole of monomer.

The solvent should be an organic solvent which is inert to the reactants. It must also have a boiling point which is above that of the catalyzed reaction of the monomer. A solvent with a boiling point above the temperature of the reaction of the monomer and the bis(dialkylamino)methane is preferred; generally this requires a boiling point above about 150° C. A preferred solvent is 1,2,4-trimethylbenzene. With reactions involving 1 mole of monomer, about 300 to 400 g of this solvent is preferably used. Various other hydrocarbons, including mineral spirits may also be used as the solvent. Generally, the amount of solvent used ranges from ½ to 3 times the weight of the monomer with about a 1:1.0–1.5 weight ratio of monomer to solvent preferred.

In reaction (iii) the products of reactions (i) and (ii) are combined. Generally the bis(dialkylamino)methane and the monomer are used in roughly stoichiometric amounts, i.e. about two moles of monomer are used for each mole of bis(dialkylamino)methane. Preferably a molar excess of the bis(dialkylamino)methane is used. A suitable molar ratio of monomer to bis(dialkylamino)methane is about 1:0.5 to 0.75, preferably about 1:0.63. The catalyzed reaction is effected by heating the mixture to a temperature high enough to drive the reaction, generally about 150° C. The reaction is allowed to proceed to completion—generally about six to fourteen hours. A reaction time of 10 hours has been found preferable where 1 mole of the monomer 6-benzotriazolyl-4-(1,1,3,3-tetramethylbutyl)-phenol (i.e. 323 grams) is used.

The mixture resulting from the catalyzed reaction is a semisolid. It is cooled and neutralized with a suitable organic acid. Glacial acetic acid is preferred. However, other acids, particularly carboxylic acids such as propionic acid, formic acid and trifluoroacetic acid are also suitable.

In order to remove the salt formed in the reaction of the neutralizing acid, it is preferred that a solvent for the salt be added to the reaction mixture. The bis-phenol should not be soluble in the solvent selected. The solvent need only be added in an amount sufficient to render the mixture stirrable. Typically, the amount of solvent will be 1 to 5 times the weight of the monomer used. Lower alkanols (i.e., alkanols having one to ten carbons) are suitable solvents for this purpose, with methanol being preferred. Acetone is a preferred solvent for the benzophenone reaction.

2,2'-Methylene-bis-[6-(2H-benzotriazol-2-yl)-4-(alkyl or alkoxy)-phenol] or 5,5'-methylene bis(2-hydroxy-4-alkoxy benzophenone) simply precipitates from this reaction mixture and can be recovered by centrifugation or filtration as a powder. Products having a purity greater than 90 and as high as 99.4% are achieved with the process of the invention.

The following examples are illustrative of the invention.

EXAMPLE I a) Preparation of Bis-(dipropylamino)methane 231 g (2.28 moles) of dipropylamine and 30 g (1 mole) of paraformaldehyde were heated to 120° C. with stirring until no more water was collected, about one to two hours. The temperature was then lowered to 50° C. By applying vacuum (15–20 psi) and increasing the temperature to 120° C., the excess of dipropylamine was removed. 202 g of bis-(dipropylamino)methane was collected. (Yield=100%). Boiling point of the product was 215°–225° C. or 115° C./15 mm of Hg.

b) Preparation of 2,2'-Methylene bis (4-t-octyl-6-benzotriazolylphenol)

4-t-Octyl-6-benzotriazolylphenol 323 g (1 mole) was dissolved in 323 g of pseudocumene at 60°–80° C. 4 g (0.1 mole) of sodium hydroxide was added and the mixture was heated to 150° C. to remove all water (about ½ to one hour). 128 g (0.63 mole) of bis- (dipropylamino)methane produced in step (a) was added and the mixture was heated at 150° C. for 12 hours with constant removing of dipropylamine. At 110° C., 60 g of glacial acetic acid was added and the mixture was refluxed for 30 minutes. Later, it was cooled down to 50° C. and 300 g of methanol was added. The mixture was filtered off at 10°–15° C. 256 g of product was obtained. (Yield=78%). The melting point was 194°–196° C. and the purity by HPLC was 99.4%.

EXAMPLE II

Preparation of 5,5'-Methylene bis-(2-hydroxy-4-methoxybenzophenone)

22.8 g (0.1 mole) of 2-Hydroxy-4-methoxybenzophenone was dissolved in 30 g of pseudocumene. 0.4 g (0.01 mole) of sodium, hydroxide was added and this mixture was heated to 150° C. to remove water. Then, 12.8 g (0.063 mole) of bis(dipropylamino)methane prepared according to step (a) of Example I was added and the mixture was heated at 150° C. for 12 hours with removal of dipropylamine. 5 g of glacial acetic acid was then added and the mixture was refluxed for 30 minutes. Later, it was cooled down to 50° C. and 30 ml of acetone was added. The precipitated product was filtered off. 17.5 g of yellow powdered product which melted at 227°–229° C. was recovered. (Yield=75%)

What is claimed is:

1. A method for preparing a compound of formula I

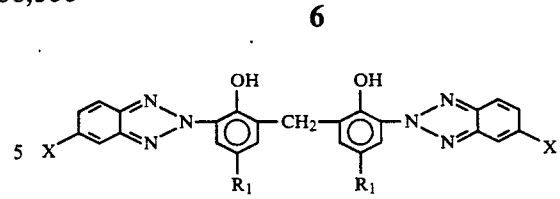

wherein $R_1$ is an alkyl group of one to twelve carbons or a cycloalkyl group of five to eight carbons, and X is chloro or hydrogen comprising:

(a) mixing an alkaline catalyst and a monomer of Formula III

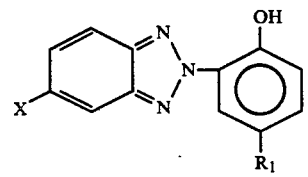

with heating at a temperature high enough to drive off the liquid formed in the reaction, (b) combining the products of step (a) with a bis(-dialkylamino)methane of the formula $CH_2(NR_3R_4)_2$ in which $R_3$ and $R_4$ are independently alkyl groups having three or more carbons and stirring the mixture at a temperature sufficient to drive the reaction for six to fourteen hours, and (c) thereafter collecting the resulting compound of Formula I.

2. The method of claim 1 wherein $R_1$ is 1,1,3,3-tetramethylbutyl and X is hydrogen.

3. The method of claim 1 in which the bis(dialkylamino)methane is manufactured by reacting a dialkylamine of the formula $HNR_3R_4$ wherein $R_3$ and $R_4$ are independently alkyl groups having three or more carbons and a solid formaldehyde material to produce the corresponding bis(dialkylamino)methane.

4. The method of claim 3 wherein $R_3$ and $R_4$ are propyl.

5. The method of claim 3 wherein $R_3$ and $R_4$ are n-propyl.

6. The method of claim 3 wherein the solid formaldehyde material is paraformaldehyde.

7. The method of claim 3 wherein about two to three moles of dialkylamine are used for each mole of carbon in the formaldehyde material.

8. The method of claim 3 wherein the reactants are heated to 95° to 130° C. during reaction of the dialkylamine and the formaldehyde.

9. The method of claim 1 wherein about 0.5 to 0.75 mole of bis-(dialkylamino)methane is used for each mole of monomer.

10. The method of claim 1 wherein the catalyst is selected from the group consisting of a lower alkali metal alcoholate, an alkali metal hydroxide, an alkali metal amide and an alkaline salt.

11. The method of claim 1 wherein the catalyst is sodium hydroxide.

12. The method of claim 1 wherein about 0.1 mole of catalyst is used for each mole of monomer used.

13. The method of claim 1 wherein a solvent is added in step (a).

14. The method of claim 13 wherein the solvent is pseudocumene.

15. The method of claim 1 wherein step (b) is conducted at at least 150° C.

16. The method of claim 1 wherein an organic acid is used to neutralize the mixture following steb (b).

17. The method of claim 16 wherein the organic acid is glacial acetic acid.

18. The method of claim 3 wherein:
(i) the relative proportions of reactants used to manufacture the bis(dialkylamino)methane are about 2 moles of dialkylamine per mole of carbon in the formaldehyde and such reactants are mixed and heated to 120° to 130° C. for one to two hours,
(ii) the molar ratio of monomer to catalyst is about 1:0.1 and the monomer and catalyst are mixed in step (a) in an inert solvent having a boiling point above 150° C.,
(iii) about 0.5 to 0.75 mole of the bis(dialkylamino)methane product is combined with each mole of the product of step (a) and the reaction is stirred in step (b) for about ten hours at a temperature of about 150° C., and
(iv) the reaction is neutralized with an organic acid in step (c).

* * * * *

UNITED STATES PATENT AND TRADEMARK OFFICE
CERTIFICATE OF CORRECTION

PATENT NO. : 5,166,355
DATED : November 24, 1992
INVENTOR(S) : Leistner et al.

It is certified that error appears in the above-indentified patent and that said Letters Patent is hereby corrected as shown below:

On the title page:

Please add to [75] Inventors: Arvind Mathur, Jersey City, NJ.

Signed and Sealed this

Twelfth Day of October, 1993

*Attest:*

BRUCE LEHMAN

*Attesting Officer*  *Commissioner of Patents and Trademarks*